US00PP13433P2

(12) United States Plant Patent
Smith

(10) Patent No.: US PP13,433 P2
(45) Date of Patent: Dec. 31, 2002

(54) CEANOTHUS PLANT NAMED 'PERADO'

(75) Inventor: Simon Smith, Littlehampton (GB)

(73) Assignee: Yoder Tuddington, Littlehampton (GB)

( * ) Notice: Subject to any disclaimer, the term of this patent is extended or adjusted under 35 U.S.C. 154(b) by 0 days.

(21) Appl. No.: 09/940,162

(22) Filed: Aug. 24, 2001

(51) Int. Cl.[7] ..... A01H 5/00
(52) U.S. Cl. ..... Plt./226

(58) Field of Search ..... Plt./226

*Primary Examiner*—Bruce R. Campell
*Assistant Examiner*—June Hwu
(74) *Attorney, Agent, or Firm*—Mark P. Bourgeois

(57) ABSTRACT

A new cultivar of Ceanothus named 'Perado' that is characterized by an upright habit, small rounded pale blue flowers, variegated foliage with large dark green centers, and increased vigor over other variegated varieties, setting it apart from all other existing varieties of Ceanothus.

2 Drawing Sheets

LATIN NAME OF THE GENUS AND SPECIES OF THE CLAIMED PLANT

*Ceanothus thyrsiflorus.*

VARIETY DENOMINATION

'Perado'.

BACKGROUND OF THE INVENTION

The present invention relates to a new and distinct cultivar of Ceanothus known botanically as a *Ceanothus thyrsiflorus* and referred to hereinafter by the cultivar name 'Perado'. The parent plant *Ceanothus thyrsiflorus* 'Zanzibar' (unpatented) was discovered at Pershoe College of Horticulture as a sport of *Ceanothus thyrsiflorus*. The present invention was discovered by the inventor in August 1996 at Littlehampton, England as a single naturally occurring branch sport on a plant of 'Zanzibar' amongst a large crop being grown for retail sales.

'Perada' is an evergreen shrub distinguished by golden yellow variegated foliage, small round pale blue flowers and increased vigor over other variegated varieties. The closest comparison plant is the parent 'Zanzibar'. The new invention is distinguishable from the parent plant by increased vigor, smaller flowers, variegated leaves that exhibit large irregularly shaped dark green centers with golden yellow margins, and stiff lateral branches that grow out at a 45° angle, in contrast to 'Zanzibar' which exhibits branches that arch over in a lax habit.

The new cultivar was first asexually propagated by the inventor at Littlehampton, England in 1996. Asexual propagation was accomplished using vegetative tip cuttings. Since that time, under careful observation, successive generations have been determined stable and uniform.

SUMMARY OF THE INVENTION

The following represent the distinguishing characteristics of the new Ceanothus cultivar 'Perado'. In combination these traits set 'Perado' apart from all other existing varieties of Ceanothus. 'Perado' has not been tested under all possible conditions and phenotypic differences may be observed with variations in environmental, climatic, and cultural conditions, however, without any variance in genotype.

1. Ceanothus 'Perado' exhibits variegated foliage with large, irregular dark green centers and golden yellow margins.

2. Ceanothus 'Perado' exhibits increased vigor over the parent plant as well as other variegated varieties of Ceanothus.

3. Ceanothus 'Perado' exhibits small rounded, pale blue flower heads in spring.

4. Ceanothus 'Perado' exhibits an upright habit with stiff lateral branches growing out at a 45° angle.

5. Ceanothus 'Perado' is 2 meters in width and 4 meters in height at maturity.

6. Ceanothus 'Perado' is hardy to minus 6° Centigrade.

BRIEF DESCRIPTION OF THE DRAWINGS

The accompanying color photographs illustrate the distinguishing traits of the new cultivar. The plants in the photographs were grown outside in Arroyo Grande, Calif. in seven-gallon containers.

The photograph on sheet 1 illustrates the new cultivar in bloom from a side perspective.

The photograph on sheet 2 is a comparison photograph showing 'Perado' and 'Zanzibar' (prior art) side by side and illustrating the differences in foliage and branching. The vigor is also illustrated in the photograph on sheet 2, showing both plants in seven-gallon containers grown under the same cultural environmental conditions. 'Perado' on the left is 18 months and 'Zannibar' on the right is 24 months. The larger and more vigorous plant is 'Perado' which was planted six months after 'Zannzibar'. All photographs are taken using conventional techniques and although foliage colors may appear different from actual colors due to light reflectance, they are as accurate as possible by conventional photography.

BOTANICAL DESCRIPTION OF THE PLANT

The following is a detailed description of the Ceanothus cultivar named 'Perado'. Data was collected in Arroyo Grande, Calif. from plants grown in seven-gallon containers out of doors. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. The growing requirements are similar to the species.

Botanical classification: *Ceanothus thyrsiflorus* 'Perado'.
Common name: Wild lilac or blue blossom.
Use: Accent, specimen in container or massed in the landscape.
Parent: 'Perado' is a naturally occurring branch sport of *Ceanothus thyrsiflorus* 'Zanzibar'.
Growth rate: Vigorous.
Habit: Dense and mounded clumps.
Height (at maturity): 4 meters in height.
Width (at maturity): 2 meters in width.
Hardiness: Hardy to minus 6° Centigrade.
Propagation: 'Perado' is propagated by vegetative tip cuttings. Root system: Vigorous and fibrous. Soil: Plant in well-drained soils. Sunlight: Plant in full sun. Type: Evergreen shrub. Special needs: Pinching back may encourage fullness. Time to initiate roots: Approximately six weeks are required for an initial cutting to produce roots.
Crop time: Approximately six to nine months is required to produce a finished one-gallon container from a rooted cutting.
Branching habit: Upright and ascending with branches at 45° angles.
Susceptibility to insects or disease: 'Perado' is susceptible to aphids and water molds.
Seasonal interest: Pale blue flowers in spring and variegated foliage year round.
Stem:
*Presence of thorns or stipules.*—None.
*Internode length.*—3 cm. between nodes.
*Stem length.*—10.5 cm. in length.
*Shape.*—Alate.
*Surface.*—Puberulent.
*Color.*—146A.
Foliage:
*Leaf arrangement.*—Alternate.
*Leaf division.*—Simple.
*Leaf shape.*—Ovate.
*Leaf base.*—Aequilateral.
*Leaf tip.*—Rounded.
*Leaf venation.*—Palmate with three prominent veins depressed on the adaxial surface and protruding on the abaxial surface.
*Vein color* (*adaxial surface*).—146C.
*Vein color* (*abaxial surface*).—146C.
*Leaf surface* (*adaxial*).—Glabrous.
*Leaf surface* (*abaxial*).—Glaucescent.
*Leaf attachment.*—Short-petiolate.
*Petiole dimensions.*—6 mm. in length and 1 mm. in width.
*Petiole surface.*—Puberulent.
*Leaf margin.*—Crenate and sparsely serrate.
*Leaf length.*—2.5 cm in length.
*Leaf width.*—1.25 cm in width.
*Quantity of leaves.*—Approximately 46 leaves per stem and 5 leaves per node.
*Leaf color* (*adaxial surface*).—Large irregular centers that are 147A and yellow-green margins that are 153D.
*Leaf color* (*abaxial surface*).—Large irregular green centers that are 146A and yellow-green margins that are 153B.
*Foliar fragrance.*—Absent.
Flower:
*Form.*—Raceme.
*Dimensions of raceme.*—11 cm. in length and 1.5 cm. in width.
*Shape.*—Campanulate.
*Sexuality.*—Monecious.
*Aspect.*—Facing outward.
*Color of flower petal.*—95D.
*Petals.*—Five in number.
*Petal shape.*—Spatulate.
*Petal surface.*—Smooth.
*Petal length.*—2.75 mm in length.
*Petal width.*—Less than 1 mm in width.
*Unfused or fused.*—Petals are unfused.
*Bud color.*—95C.
*Bud shape.*—Globose.
*Bud dimensions.*—2.50 mm. in length and 2.75 mm. in diameter.
*Dimensions of open flower.*—3 mm. in diameter and 3 mm. in length
*Persistent or self-cleaning.*—Self-cleaning.
*Shape of calyx.*—Globose when closed and stellate when open.
*Color of calyx.*—95C.
*Dimensions of calyx.*—3 mm. in diameter and 2 mm. in length.
*Number of sepals.*—Five sepals.
*Sepal color.*—95C.
*Dimensions of sepal.*—Less than 0.75 mm. in width and 2 mm. in length.
*Blooming period.*—Spring.
*Quantity of flowers.*—Approximately 64 per peduncle.
*Peduncle.*—Extended with internodes of 1.25 cm. in length between nodes.
*Color of peduncle.*—144 A.
*Surface of peduncle.*—Puberulent.
*Fragrance.*—Faintly sweet.
Reproduction organs:
*Stamens.*—Five in number.
*Form of stamen.*—Filament with crinkled apex.
*Color of filament.*—95D.
*Dimensions of stamen.*—4 mm. in length and less than 0.25 mm in diameter.
Anther color.—158D.
*Dimensions of anther.*—1 mm. in width and 1 mm. in length.
*Pollen color.*—158D.
*Pistil.*—One in number.
*Dimensions of pistil.*—3 mm. in length and less than 0.50 mm. in diameter.
*Stigma shape.*—Trifid.
*Stigma color.*—161A.
*Dimensions of stigma.*—1 mm. in height and 1.25 mm. in diameter.
*Style color.*—95C.
*Style dimensions.*—1 mm. in length and less than 0.50 mm. in diameter.
*Ovary position.*—Superior.
*Ovary color.*—202A.
*Ovary dimensions.*—2 mm. in diameter and 1 mm. in height.
*Ovary shape.*—Globose.
Seed: Seed production has not been observed.

I claim:
1. A new and distinct variety of Ceanothus plant named 'Perado' as described and illustrated.

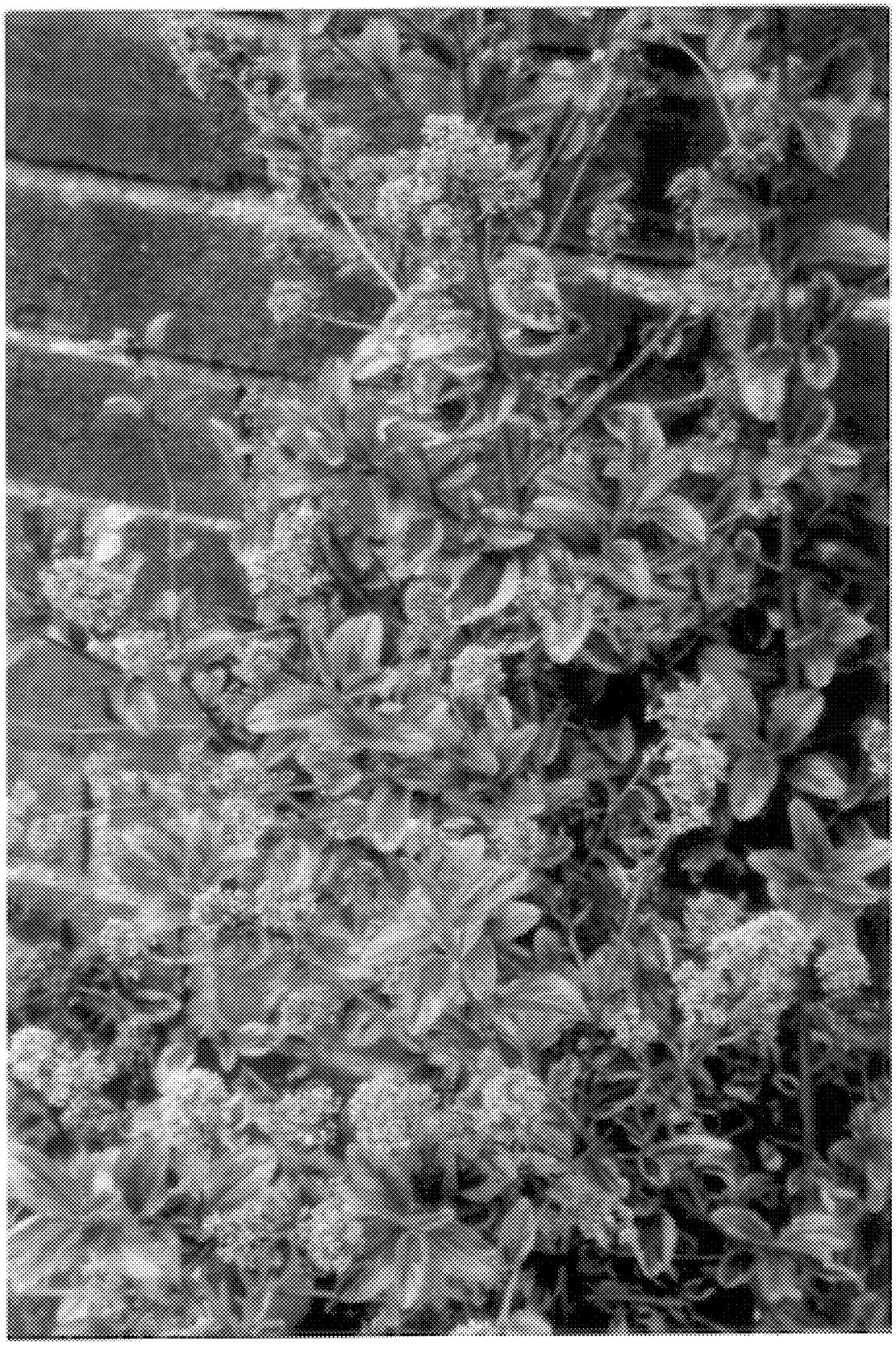

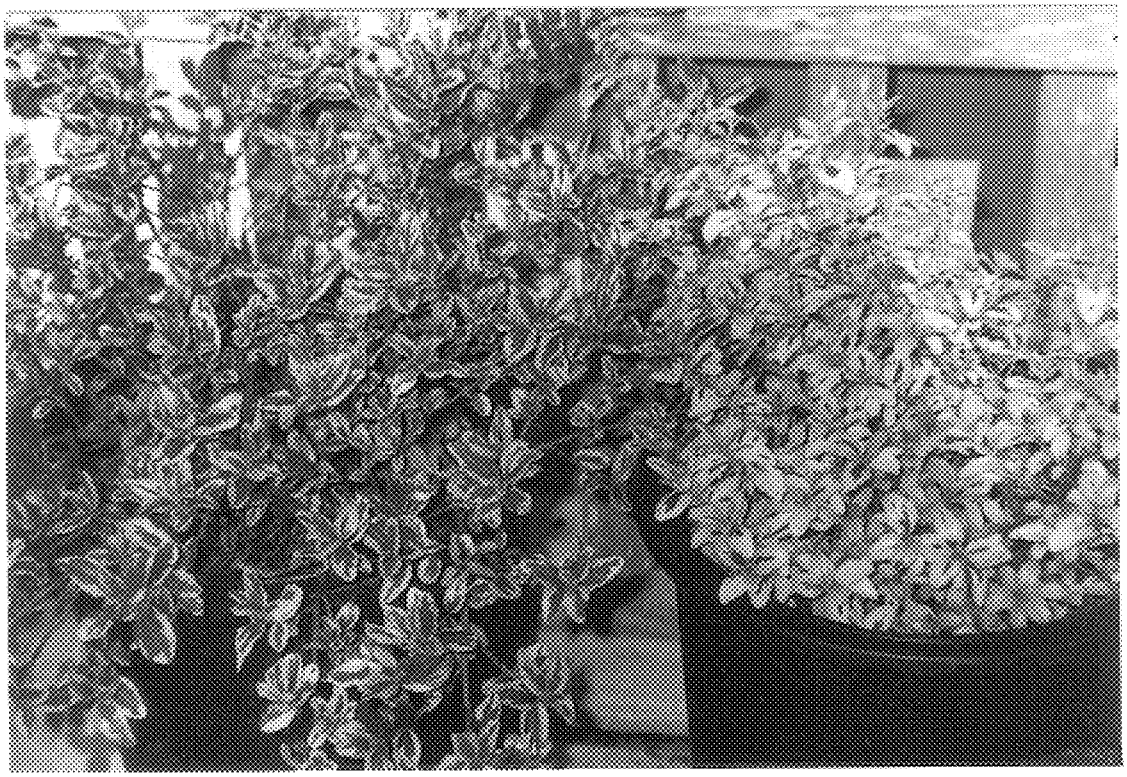

* * * * *